United States Patent
Shaw et al.

(10) Patent No.: US 11,476,002 B2
(45) Date of Patent: Oct. 18, 2022

(54) CLINICAL RISK MODEL

(71) Applicant: Flatiron Health, Inc., New York, NY (US)

(72) Inventors: Pooja Shaw, New York, NY (US); Abigail Orlando, New York, NY (US); Alexander Rich, New York, NY (US); Rebecca Miksad, Newton, MA (US); Dominique Connolly, Lincroft, NJ (US); Blythe Adamson, New York, NY (US); Jessie Tseng, New York, NY (US); Maya Najarian, Denver, CO (US); Shreyas Lakhtakia, New York, NY (US); Joshua Kraut, Seattle, WA (US); Jesse Lee, New York, NY (US)

(73) Assignee: FLATIRON HEALTH, INC., New York, NY (US)

( * ) Notice: Subject to any disclaimer, the term of this patent is extended or adjusted under 35 U.S.C. 154(b) by 20 days.

(21) Appl. No.: 17/119,390

(22) Filed: Dec. 11, 2020

(65) Prior Publication Data

US 2021/0296000 A1     Sep. 23, 2021

Related U.S. Application Data

(60) Provisional application No. 63/106,539, filed on Oct. 28, 2020, provisional application No. 62/990,933, filed on Mar. 17, 2020.

(51) Int. Cl.
*G16H 50/30*     (2018.01)
*G16H 10/60*     (2018.01)
(Continued)

(52) U.S. Cl.
CPC ............ *G16H 50/30* (2018.01); *G06N 20/00* (2019.01); *G16H 10/40* (2018.01); *G16H 10/60* (2018.01);
(Continued)

(58) Field of Classification Search
None
See application file for complete search history.

(56) References Cited

U.S. PATENT DOCUMENTS

| 10,650,928 | B1* | 5/2020 | Larson .................. G16H 50/20 |
| 2007/0055552 | A1 | 3/2007 | St. Clair et al. |
| 2013/0132323 | A1* | 5/2013 | Soto ...................... G06Q 40/08 706/46 |
| 2016/0171177 | A1 | 6/2016 | Caffarel et al. |
| 2016/0358282 | A1* | 12/2016 | Gopal .................... G16H 10/60 |

(Continued)

OTHER PUBLICATIONS

Fenlon et al., A discussion of calibration techniques for evaluating binary and categorical predictive models, 2018, Preventative Veterinary Medicine 149, 107-114 (Year: 2018).*

(Continued)

*Primary Examiner* — Christopher L Gilligan
*Assistant Examiner* — Karen A Hranek
(74) *Attorney, Agent, or Firm* — Finnegan, Henderson, Farabow, Garrett & Dunner, LLP

(57) ABSTRACT

A model-assisted system and method for predicting health care services. In one implementation, a model-assisted system may comprise a least one processor programmed to access a database storing a medical record associated with a patient and analyze the medical record to identify a characteristic of the patient. The processor may determine a patient risk level indicating a likelihood that the patient will require a health care service within a predetermined time period; compare the patient risk level to a predetermined risk threshold; and generate a report indicating a recommended intervention for the patient. The processor may further determine a calibration factor indicating a difference between an average patient risk level and an average actual (Continued)

healthcare service usage for a first group of patients; and determine, based on the calibration factor, a bias relative to a second group of patients.

19 Claims, 8 Drawing Sheets

(51) Int. Cl.
  *G16H 50/70* (2018.01)
  *G06N 20/00* (2019.01)
  *G16H 70/00* (2018.01)
  *G16H 10/40* (2018.01)
  *G16H 50/20* (2018.01)

(52) U.S. Cl.
  CPC ............. *G16H 50/20* (2018.01); *G16H 50/70* (2018.01); *G16H 70/00* (2018.01)

(56) References Cited

U.S. PATENT DOCUMENTS

| | | | |
|---|---|---|---|
| 2017/0293858 A1* | 10/2017 | Larsen | G06Q 30/02 |
| 2018/0285691 A1* | 10/2018 | Grindstaff | G06Q 10/04 |
| 2019/0034590 A1 | 1/2019 | Oren et al. | |
| 2019/0034591 A1 | 1/2019 | Mossin et al. | |
| 2019/0043070 A1* | 2/2019 | Merrill | G06N 5/04 |
| 2019/0237201 A1* | 8/2019 | Bauman | G16H 40/60 |
| 2020/0005900 A1* | 1/2020 | Cha | G16H 50/20 |
| 2020/0082299 A1* | 3/2020 | Vasconcelos | G06N 5/045 |
| 2020/0132884 A1* | 4/2020 | Rothenberg | G06N 7/005 |
| 2020/0151555 A1* | 5/2020 | Kozhaya | G06N 3/08 |
| 2020/0160180 A1* | 5/2020 | Lehr | G06N 3/08 |
| 2020/0184350 A1* | 6/2020 | Bhide | G06N 20/20 |
| 2020/0242566 A1* | 7/2020 | Agarwal | G06Q 10/1095 |
| 2020/0380398 A1* | 12/2020 | Weider | G06N 20/00 |
| 2021/0082577 A1* | 3/2021 | Sharifi | G06N 20/00 |

OTHER PUBLICATIONS

Huang et al., A tutorial on calibration measurements and calibrationmodels for clinical prediction models, Feb. 27, 2020, Journal of the American Medical Informatics Association, 27(4), 621-633 (Year: 2020).*

Hardt et al., Equality of Opportunity in Supervised Learning, Oct. 7, 2016 (Year: 2016).*

Pleiss et al, On Fairness and Calibration, 2017, 31st Conference on Neural Information Processing Systems (Year: 2017).*

Lee et al., Algorithmic bias detection and mitigation: Best practices and policies to reduce consumer harms, May 22, 2019, Brookings (Year: 2019).*

Barocas et al., Fairness in Machine Learning, Feb. 21, 2020, p. 37-72 & 121-157 (Year: 2020).*

Kleinberg et al., Inherent Trade-Offs in the Fair Determination of Risk Scores, 2017, 8th Innovations in Theoretical Computer Science Conference (Year: 2017).*

Bellamy et al., AI Fairness 360: An Extensivel Toolkit for Detecting, Understanding, and Mitigating Unwanted Algorithmic Bias, Oct. 2018, IBM J Res Dev 2019 (Year: 2018).*

Ewout W. Steyerber et al., "Assessing the performance of prediction models: a framework for some traditional and novel measures," Epidemiology, Jan. 2010, pp. 128-138.

Ziad Obermeyer et al., "Dissecting racial bias in an algorithm used to manage the health of populations," Science, Oct. 25, 2019, vol. 366, pp. 447-453.

Sam Corbett-Davis et al., "The Measure and Mismeasure of Fairness: A Critical Review of Fair Machine Learning," Sep. 11, 2018 (25 pages).

International Search Report and Written Opinion in International Application No. PCT/US2020/064509, dated Mar. 29, 2021 (13 pgs.).

* cited by examiner

Top Positive Risk Predictors Summary

| Patient Name | Date of Birth | Gender | Vitals — Weight | Labs — Out of range albumin lab result in past 30 days? | Orders — Antiemetic order in past 90 days? | Visits — Greater than 3 ED visits in past 90 days? | Diagnosis: Atrial Fibrillation | Diagnosis — Cancer Diagnosis: Ovary | Diagnosis — Cancer Diagnosis: Secondary Malignant |
|---|---|---|---|---|---|---|---|---|---|
| "Patient 1" | 04/07/1956 | F | X |   |   | X | X | X | X |
| "Patient 2" | 01/19/1961 | F |   | X |   | X | X |   | X |
| "Patient 3" | 08/14/1969 | F |   | X |   | X |   |   | X |
| "Patient 4" | 02/14/1955 | M | X |   | X | X | X |   |   |
| "Patient 5" | 09/20/1972 | M |   |   |   | X | X |   | X |

CLINICAL RISK MODEL

CROSS-REFERENCES TO RELATED APPLICATIONS

This application claims the benefit of U.S. Provisional Application No. 62/990,933, filed on Mar. 17, 2020, and U.S. Provisional Application No. 63/106,539, filed on Oct. 28, 2020, the contents of which are incorporated herein by reference in their entirety.

BACKGROUND

Technical Field

The present disclosure relates to predicting medical care for patients and, more specifically, to a model-assisted system and method for predicting and planning for specific types of health care services for patients and/or types of clinical outcomes.

Background Information

In today's health care system, significant benefits may potentially be realized by reducing the likelihood that certain individuals or patients will need to make use of certain types of health care services (e.g., emergency or hospital room visits, ambulance transportation, emergency or acute treatments, hospital-based or other urgent care services, etc.). For example, certain types of health care services, such as hospital or other acute care services, may be more costly (and often significantly more costly) and also desirable to avoid, than other types of health care services, for example, services delivered in locations outside of high cost hospital or urgent care centers, such as physician office visits, home care visits, etc. Thus, reducing patients' needs to make use of certain types of health care services may have the potential to significantly reduce health care costs for individuals, insurers, group health insurance policy holders, among others, while also increasing the quality of care delivered to patients. For example, reducing the likelihood that one or more patients needs to take advantage of hospitals or acute care may reduce the load on such services and may free up hospital-based and acute care resources for other patients. Additionally, reducing or eliminating patients' needs for hospital visits, etc., may reduce the likelihood that such patients are exposed to infectious diseases that may be contracted from other hospital patients. Such a benefit may be especially important to certain types of patients (e.g., cancer patients, etc.) with compromised immune systems. Note, the term hospital, as used herein, includes hospitals and other urgent care facilities.

One effective way to potentially reduce the likelihood for patient reliance upon certain types of health care services is to identify those patients with the highest likelihood for such future health care service usage and preemptively offer medical treatment, care, or other interventions (e.g., phone calls, sending prescriptions to pharmacies, electronic communications/reminders, referral to specialist, etc.) to those patients. For example, health care entities may deploy health care professionals to provide preemptive care to any number of patients ranging from a handful of patients (e.g., ten patients) to many patients (e.g., two thousand patients). When scheduling health care professionals and/or interventions to provide preemptive care (e.g., home visits, phone calls, sending prescriptions to pharmacies, treatment, electronic communications/reminders etc.), health care entities may wish to prioritize patients most at risk for certain types of health care services in the near term to reduce the need for such health care services. For example, if a health care entity can identify that a patient is dehydrated or needs pain medication (among a variety of other conditions that may lead to an eventual visit to an emergency room or use of other hospital or acute care services), scheduling a health care professional, or other intervention, to care for the patient may help minimize or even avoid the need for such hospital or acute care services. Identifying patients that are at high risk for certain types of health care services or identifying patient at high risk for certain clinical outcomes (e.g., mortality, febrile neutropenia, depression), and scheduling health care processionals' and/or other interventions, to provide preemptive care to those patients, in a proactive, preventive manner may thus improve the care of patients and provide more targeted treatments to patients. Importantly, such patient identification and proactive interventions may significantly reduce the likelihood that such patients will make use of hospital or acute care, or suffer undesirable clinical outcomes, which may result in any or all of the benefits discussed above, among others.

Preemptively identifying those patients most likely to take advantage of hospital or other types of health care services, or patients who are at risk for certain clinical outcomes, however, can be challenging. The typical source of information regarding a patient and the health of that patient is the patient's medical chart, which may be maintained as an electronic health record (EHR). However, it is time consuming and inefficient (and in many cases impossible due to the sheer number of patients and the time involved to review each chart) to manually and continuously review the charts of each patient in order to identify and prioritize those patients most likely to access hospital-based or other types of health services (e.g., within a certain time period) or at risk for certain clinical outcomes. Moreover, in many cases, human reviewers may be incapable of recognizing patterns, markers, etc., in an EHR or other medical chart indicative of a patient's likely use of hospital or other health care services or a patient who is at risk for certain clinical outcomes within a certain time period (e.g., 1 week, 30 days, 60 days, 90 days, etc.). Accordingly, even if there was time to manually review (such as on an ongoing basis) the medical charts and health records for an entire patient population, such a review would likely be ineffective in identifying a suitable population of those patients most likely to make use of such health care services. Thus, there is a need for a technical system to more efficiently and effectively analyze patient records and identify patients most likely to make near term use of certain types of health care services or patients who are at near term risk for certain clinical outcomes.

SUMMARY

Embodiments consistent with the present disclosure include systems and methods for predicting health care services. In an embodiment, a model-assisted system may comprise a least one processor. The processor may be programmed to access a database storing medical records associated with a plurality of patients and analyze a medical record associated with a patient of the plurality of patients to identify a characteristic of the patient. The processor may determine, based on the patient characteristic and using a trained machine learning model, a patient risk level indicating a likelihood that the patient will require a health care service within a predetermined time period, the machine learning model being trained based on clinical factors weighted based on an logistic regression. The processor may further compare the patient risk level to a predetermined risk threshold; generate, based on the comparison, a report indicating a recommended intervention for the patient; determine a calibration factor indicating a difference between an average patient risk level and an average actual healthcare service usage for a first group of the plurality of patients; and determine, based on the calibration factor, a bias associated with the first group relative to a second group of the plurality of patients.

In another embodiment, a computer-implemented method for predicting health care services is disclosed. The method may comprise accessing a database storing medical records associated with a plurality of patients and analyzing a medical record associated with a patient of the plurality of patients to identify a characteristic associated with the patient. The method may comprise determining, based on the patient characteristic and using a trained machine learning model, a patient risk level indicating a likelihood that the patient will require a health care service within a predetermined time period, the machine learning model being trained based on clinical factors weighted based on logistic regression. The method may further comprise comparing the patient risk level to a predetermined risk threshold; generating, based on the comparison, a report indicating a recommended intervention for the patient; determining a calibration factor indicating a difference between an average patient risk level and an average actual healthcare service usage for a first group of the plurality of patients; and determining, based on the calibration factor, a bias associated with the first group relative to a second group of the plurality of patients.

In an embodiment, a system for evaluating bias in a machine learning model may comprise a least one processor. The processor may be programmed to receive a plurality of outputs from a machine learning model, the outputs comprising predictions for a plurality of patients based on medical records associated with the plurality of patients; access a plurality of actual outcomes associated with the plurality of patients; determine a calibration factor indicating a difference between the predictions and the actual outcomes for a first group of the plurality of patients; and detect, based on the calibration factor, a bias associated with the first group relative to a second group of the plurality of patients.

Consistent with other disclosed embodiments, non-transitory computer readable storage media may store program instructions, which are executed by at least one processing device and perform any of the methods described herein.

BRIEF DESCRIPTION OF THE DRAWINGS

The accompanying drawings, which are incorporated in and constitute part of this specification, and together with the description, illustrate and serve to explain the principles of various exemplary embodiments. In the drawings:

FIG. 5 is an illustration of an example report identifying patients with heightened risk of a near-term medical visit consistent with the disclosed embodiments.

DETAILED DESCRIPTION

Figure 1:
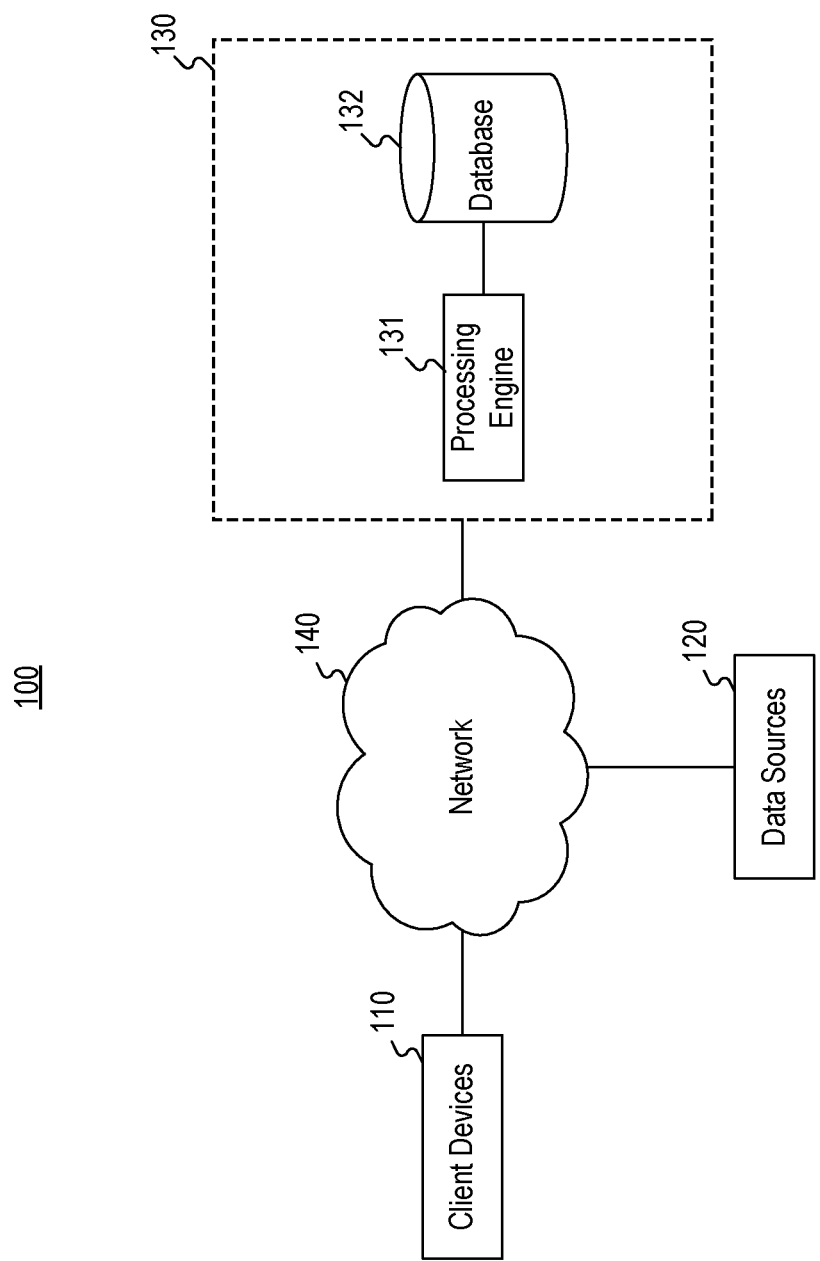
FIG. 1 is a diagram illustrating an exemplary system environment for implementing embodiments consistent with the present disclosure.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Embodiments herein include computer-implemented methods, tangible non-transitory computer-readable mediums, and systems. The computer-implemented methods may be executed, for example, by at least one processor (e.g., a processing device) that receives instructions from a non-transitory computer-readable storage medium. Similarly, systems consistent with the present disclosure may include at least one processor (e.g., a processing device) and memory, and the memory may be a non-transitory computer-readable storage medium. As used herein, a non-transitory computer-readable storage medium refers to any type of physical memory on which information or data readable by at least one processor may be stored. Examples include random access memory (RAM), read-only memory (ROM), volatile memory, nonvolatile memory, hard drives, CD ROMs, DVDs, flash drives, disks, and any other known physical storage medium. Singular terms, such as "memory" and "computer-readable storage medium," may additionally refer to multiple structures, such a plurality of memories and/or computer-readable storage mediums. As referred to herein, a "memory" may comprise any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals. In addition, as referred to herein, the terms "health service," "health care service" and "medical service" are used interchangeably.

It is understood that embodiments of the present disclosure may be used for the purpose of supporting or providing recommendations to healthcare professionals about prevention, diagnosis, or treatment of a disease or condition. Further, it is understood that embodiments of the present disclosure may enable such healthcare professionals to independently review the basis for such recommendations presented by the present disclosure, so that such healthcare professionals are primarily relying on their independent review to make a clinical diagnosis or treatment decision regarding an individual patient, and using the recommendations as supplemental information.

Embodiments of the present disclosure provide systems and methods for predicting near term use of certain types of health care services for patients (e.g., hospital or acute care) or predicting certain clinical outcomes. A user of the disclosed systems and methods may encompass any individual who may wish to access and/or analyze patient data. Thus, throughout this disclosure, references to a "user" of the disclosed systems and methods may encompass any individual, such as a physician, a healthcare administrator, a researcher, an insurance adjuster, a quality assurance department at a health care institution, and/or any other entity associated with a patient.

FIG. 1 illustrates an exemplary system environment 100 for implementing embodiments consistent with the present disclosure, described in detail below. As shown in FIG. 1, system environment 100 may include several components, including client devices 110, data sources 120, system 130, and/or network 140. It will be appreciated from this disclosure that the number and arrangement of these components is exemplary and provided for purposes of illustration. Other arrangements and numbers of components may be used without departing from the teachings and embodiments of the present disclosure.

As shown in FIG. 1, exemplary system environment 100 may include a system 130. System 130 may include one or more server systems, databases, and/or computing systems configured to receive information from entities over a network, process the information, store the information, and display/transmit the information to other entities over the network. Thus, in some embodiments, the network may facilitate cloud sharing, storage, and/or computing. In one embodiment, system 130 may include a processing engine 131 and one or more databases 132, which are illustrated in a region bounded by a dashed line representing system 130. Processing engine 131 may comprise at least one processing device, such as one or more generic processors, e.g., a central processing unit (CPU), a graphics processing unit (GPU), or the like and/or one or more specialized processors, e.g., an application-specific integrated circuit (ASIC), a field-programmable gate array (FPGA), or the like.

The various components of system environment 100 may include an assembly of hardware, software, and/or firmware, including a memory, a central processing unit (CPU), and/or a user interface. Memory may include any type of RAM or ROM embodied in a physical storage medium, such as magnetic storage including floppy disk, hard disk, or magnetic tape; semiconductor storage such as solid-state disk (SSD) or flash memory; optical disc storage; or magneto-optical disc storage. A CPU may include one or more processors for processing data according to a set of programmable instructions or software stored in the memory. The functions of each processor may be provided by a single dedicated processor or by a plurality of processors. Moreover, processors may include, without limitation, digital signal processor (DSP) hardware, or any other hardware capable of executing software. An optional user interface may include any type or combination of input/output devices, such as a display monitor, keyboard, and/or mouse.

Data transmitted and/or exchanged within system environment 100 may occur over a data interface. As used herein, a data interface may include any boundary across which two or more components of system environment 100 exchange data. For example, environment 100 may exchange data between software, hardware, databases, devices, humans, or any combination of the foregoing. Furthermore, it will be appreciated that any suitable configuration of software, processors, data storage devices, and networks may be selected to implement the components of system environment 100 and features of related embodiments.

The components of environment 100 (including system 130, client devices 110, and data sources 120) may communicate with each other or with other components through a network 140. Network 140 may comprise various types of networks, such as the Internet, a wired Wide Area Network (WAN), a wired Local Area Network (LAN), a wireless WAN (e.g., WiMAX), a wireless LAN (e.g., IEEE 802.11, etc.), a mesh network, a mobile/cellular network, an enterprise or private data network, a storage area network, a virtual private network using a public network, a nearfield communications technique (e.g., Bluetooth, infrared, etc.), or various other types of network communications. In some embodiments, the communications may take place across two or more of these forms of networks and protocols.

System 130 may be configured to receive and store the data transmitted over network 140 from various data sources, including data sources 120, process the received data, and transmit data and results based on the processing to client device 110. For example, system 130 may be configured to receive structured and/or unstructured data from one or more data sources 120 or other sources in network 140. In some embodiments, the data may include medical information stored in the form of one or more medical records. Each medical record may be associated with a particular patient. Data sources 120 may be associated with a variety of sources of medical information for a patient. For example, data sources 120 may include medical care providers of the patient, such as physicians, nurses, specialists, consultants, hospitals, clinics, and the like. Data sources 120 may also be associated with laboratories such as radiology or other imaging labs, hematology labs, pathology labs, etc. Data sources 120 may also be associated with insurance companies or any other sources of patient data (e.g., patient reported outcomes, wearable devices that track health information, public health datasets or registries).

System 130 may further communicate with one or more client devices 110 over network 140. For example, system 130 may provide results based on analysis of information from data sources 120 to client device 110. Client device 110 may include any entity or device capable of receiving or transmitting data over network 140. For example, client device 110 may include a computing device, such as a server or a desktop or laptop computer. Client device 110 may also include other devices, such as a mobile device, a tablet, a wearable device (i.e., smart watches, implantable devices, fitness trackers, etc.), a virtual machine, an IoT device, or other various technologies. In some embodiments, system 130 may further receive input or queries from client device 110. For example, client device 110 may transmit queries for information about one or more patients over network 140 to system 130, such as a query for patients likely to require near-time medical services (e.g., emergency medical services) within a particular time period, or various other information about a patient.

In some embodiments, system 130 may be configured to analyze medical records (or other forms of structured or unstructured data) of a patient or patient population to determine a risk level, a relative risk level, or any other suitable indicator of a likelihood that one or more patients will make near term use of certain type of health care services (e.g., hospital or acute care). For example, system 130 may analyze medical records of a patient to determine whether the patient will make use of specified health care services within a specific time window (e.g., the next 60 days). System 130 may be configured to use one or more machine learning models to identify these probabilities. Such systems and methods may provide value for health care entities, individuals, and others, because at risk patients may be preemptively identified and treated before escalation of one or more conditions, the occurrence of one or more medical events, or other events that may lead to use of hospital or acute health care services. Such a system, therefore, may decrease the need for hospital or acute care and/or lower the total cost of patient care, among many other potential benefits. In another example, system 130 may prioritize patients based on the type of health care service likely to be needed, where patients expected to require more serious health care services or more costly health care services are prioritized before patients expected to require less serious or less costly health care services.

System 130 may automatically analyze patient records and triage patients according to (i) a likelihood of near-term use of certain types of medical services (e.g., hospital or acute care); (ii) a likelihood of a particular near-term clinical outcome; or (iii) based on any other criteria. The system may automatically generate this information and present it for use via one or more reports, graphical user interfaces, mobile device interfaces, etc. With this information, preemptive care for patients may be planned, according to, for example: those patients most likely to make near-term use of hospital or acute medical services, those patients who are most likely to suffer particular near-term clinical outcomes, those patients for whom treatment is most likely to result in a reduced likelihood of near-term use of hospital or acute medical services (e.g., reduction in likelihood by at least a predetermined threshold amount, etc.), or any other group of patients based on a predicted impact to one or more health care services or a predicted occurrence of an undesirable clinical outcome. In some cases, system 130 may prioritize patients based on a predicted time that the patients are expected to make use of a specified health care service. For example, patients predicted to make use of hospital or acute health care service within 1-3 days may be prioritized ahead of patients predicted to make use of such services within 1-2 weeks, 1-2 months, etc.

Figure 2:
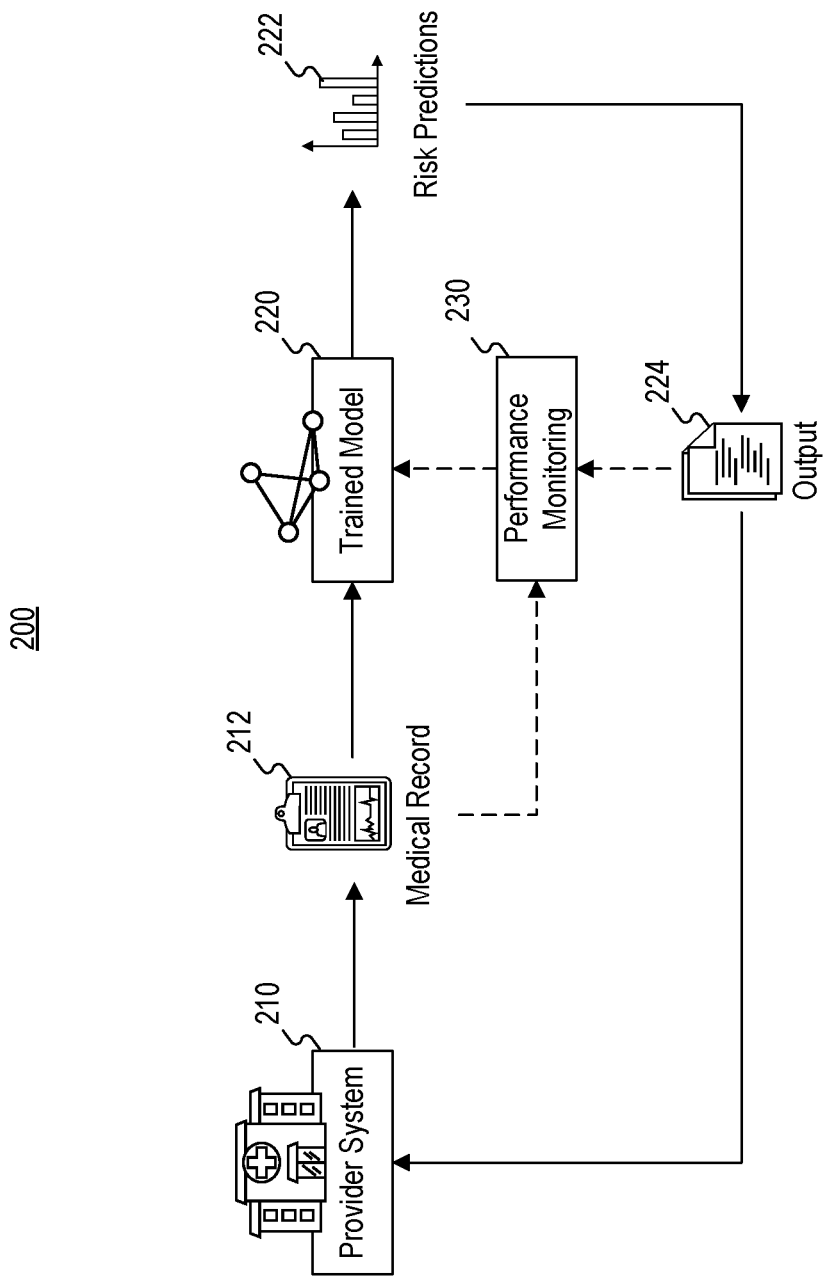
FIG. 2 is a diagram illustrating an example process for predicting health care services consistent with the disclosed embodiments.

FIG. 2 is a block diagram illustrating an example process 200 for predicting health care services or clinical outcomes consistent with the disclosed embodiments. Process 200 may include receiving medical information, such as medical record 212 from a provider system 210. Provider system 210 may include any system that may collect and/or store medical data for patients. For example, provider system 210 may include a medical care office, a hospital, a surgical center, a clinic, a lab or testing facility, a hospice center, an imaging or radiology facility, an addiction treatment facility, an urgent care facility, a rehabilitation center, a telehealth platform, an insurance facility, or any other system that may provide access to medical data. Provider system 210 may correspond to or may be associated with client devices 110 and/or data sources 120 described above.

As shown in FIG. 2, medical record 212 may be received from provider system 210. Medical record 212 may include any structured or unstructured data associated with a patient. In some embodiments, multiple medical records 212 may be received. Each patient may be represented by one or more records generated by one or more health care professionals or by the patient. For example, a doctor associated with the patient, a nurse associated with the patient, a physical therapist associated with the patient, or the like, may each generate a medical record for the patient. In some embodiments, one or more records may be collated and/or stored in the same database. In other embodiments, one or more records may be distributed across a plurality of databases. In some embodiments, the records may be stored and/or provided a plurality of electronic data representations. For example, the patient records may be represented as one or more electronic files, such as text files, portable document format (PDF) files, extensible markup language (XML) files, or the like. If the documents are stored as PDF files, images, or other files without text, the electronic data representations may also include text associated with the documents derived from an optical character recognition process. Additional details regarding medical record 212 are provided below with respect to FIG. 3.

In some embodiments, system 130 may be configured to transform this source data into a format that is interpretable by trained model 220. For example, these transformations include, but are not limited to, mapping source data to standardized formats and extracting clinical information from unstructured data using machine learning techniques. In some embodiments, medical record 212 may be associated with a request from provider system 210. For example, provider system 210 may query system 130 for near-term risk predictions for a patient or group of patients (e.g., which patients are likely to require hospital or acute care or which patients are likely to experience a particular clinical outcome). In some embodiments, medical record 212 may be provided periodically, in response to a request from system 130, any time a particular patient has an encounter with a health system (e.g., when the medical record is updated), or based on various other forms of triggers. In some embodiments, the triggers may be configurable by a user (e.g., by a system administrator, a healthcare provider system, etc.).

Medical record 212 may be input into a trained model 220, which may be configured to generate predictions for patients. Trained model 220 may be included in or otherwise associated with system 130, as described above. Trained model 220 may include any trained machine learning model configured to generate risk predictions 222 based on input data. In some embodiments, trained model 220 may include an artificial neural network. Various other machine learning algorithms may be used, including a logistic regression, a linear regression, a regression, a random forest, a K-Nearest Neighbor (KNN) model (for example as described above), a K-Means model, a decision tree, a cox proportional hazards regression model, a Naïve Bayes model, a Support Vector Machines (SVM) model, a gradient boosting algorithm, or any other form of machine learning model or algorithm. Additional details regarding the training and implementation of trained model 220 are described below with respect to FIG. 4A. Risk predictions 222 may include any information indicating a predicted near-term medical service or clinical outcome for a patient or a group of patients.

Based on the results of trained model 220, an output 224, which may indicate the risk predictions 222, may be generated and provided to provider system 210. In some embodiments, output 224 may be provided to one or more computing devices, such as client devices 110, in a physician's office, home care service, or the like, for presentation on a display associated with the one or more computing devices. For example, the reports may be displayed on one or more mobile devices for use by medical professionals. In some cases, the reports may be part of a cooperative medical care scheduling system enabling auto-scheduling and tracking of care to patients according to a predicted likelihood of near-term medical services. Accordingly, output 224 may also include scheduling preemptive care based on risk predictions 222. As noted above, a physician or other healthcare professional may review and/or accept proposed scheduling determined by the scheduling system.

Output 224 may be generated in any suitable form. In some cases, one or more reports may be generated including a list of patients to receive preemptive treatment, a list of patients organized by predicted risk for use of hospital, acute or other specified health service, a list organized according to predicted risk of using such services and a predicted time or time range when such services are expected to be pursued, or according to any other or additional criteria. In further cases, one or more reports may be generated including a list of patients who are at risk for certain clinical outcomes, a list of patients organized by predicted risk for occurrence of such outcomes, a list organized according to predicted risk of the occurrence of such outcomes and a predicted time or time range when such outcomes are likely to occur, or according to any other or additional criteria. The reports may be provided in paper form or displayed as part of a user interface. For example, the reports may identify one or more patients who have a predetermined risk level (e.g., having a risk higher than a predetermined threshold). Such reports may be available at point of care locations, in electronic health record systems, etc. Such reports may be generated according to any desired periodicity (e.g., daily, weekly, in near real time, etc.). An example report that may be generated is shown in FIG. 5 and discussed below in further detail.

Optionally, process 200 may further include a monitoring and tracking a performance of trained model 220, as shown by performance modeling 230. Performance modeling 230 may monitor one or more inputs or outputs of trained model 220, including medical record 212 and output 224. These inputs and outputs may be analyzed to assess a performance of trained model 220. In some embodiments, performance modeling 230 may access additional data, such as historical data, actual results data, or other data to assess the performance of trained model 220. For example, performance modeling 230 may be configured to identify potential biases introduced into trained model 220, as described further below with respect to FIG. 4B. In some embodiments, trained model 220 may be tuned or adjusted based on the results of performance modeling 230. Various other actions may be taken based on the results of performance modeling 230, such as generating an alert, flagging output 224, or the like. Additional details regarding performance monitoring techniques are described below with respect to FIGS. 4A and 4B.

Figure 3:
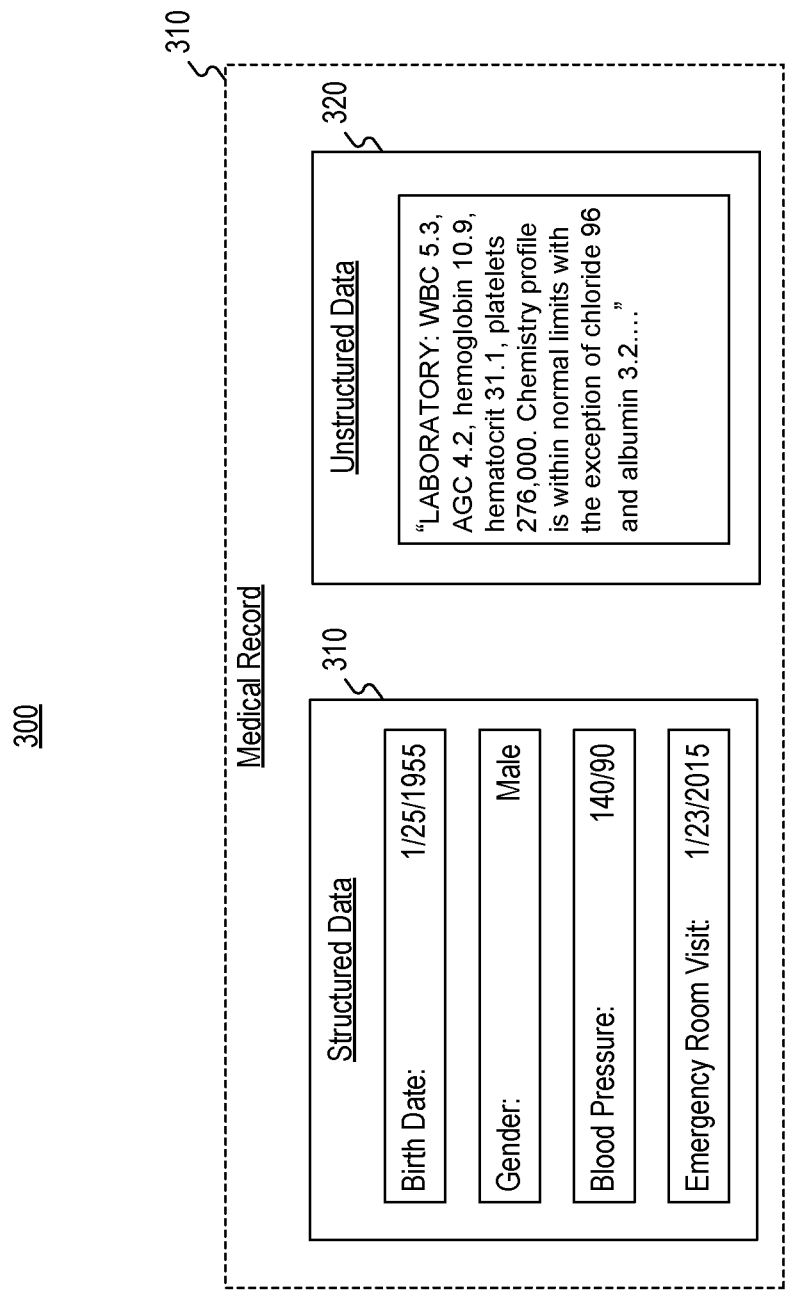
FIG. 3 illustrates an exemplary medical record for a patient consistent with the disclosed embodiments.

FIG. 3 illustrates an exemplary medical record 300 for a patient consistent with the disclosed embodiments. Medical record 300 may be received from provider system 210 and processed by trained model 220 to identify whether a patient associated medical record 300 is predicted to use near-term medical services or suffer a near-term clinical outcome. Accordingly, medical record 300 may correspond to medical record 212, described above. The records received from provider system 210 may include structured data 310 and/or unstructured data 320, as shown in FIG. 3.

Structured data 310 may include quantifiable or classifiable data about the patient, such as gender, age, race, weight, vital signs, lab results, date of diagnosis, diagnosis type, disease staging (e.g., billing codes), therapy timing, procedures performed, visit date, practice type, insurance carrier and start date, medication orders, medication administrations, or any other measurable data about the patient. Unstructured data 320 may include information about the patient that is not quantifiable or easily classified, such as physician's notes or the patient's lab reports. Unstructured data 320 may include information such as a physician's description of a treatment plan, notes describing what happened at a visit, statements or accounts from a patient, subjective evaluations or descriptions of a patient's well-being, radiology reports, pathology reports, laboratory reports, etc. Structured data 310 and/or unstructured data 320 may be processed and input into trained model 220. In some embodiments, the unstructured data may be captured by an abstraction process, while the structured data may be entered by the health care professional or calculated using algorithms.

Figure 4A:
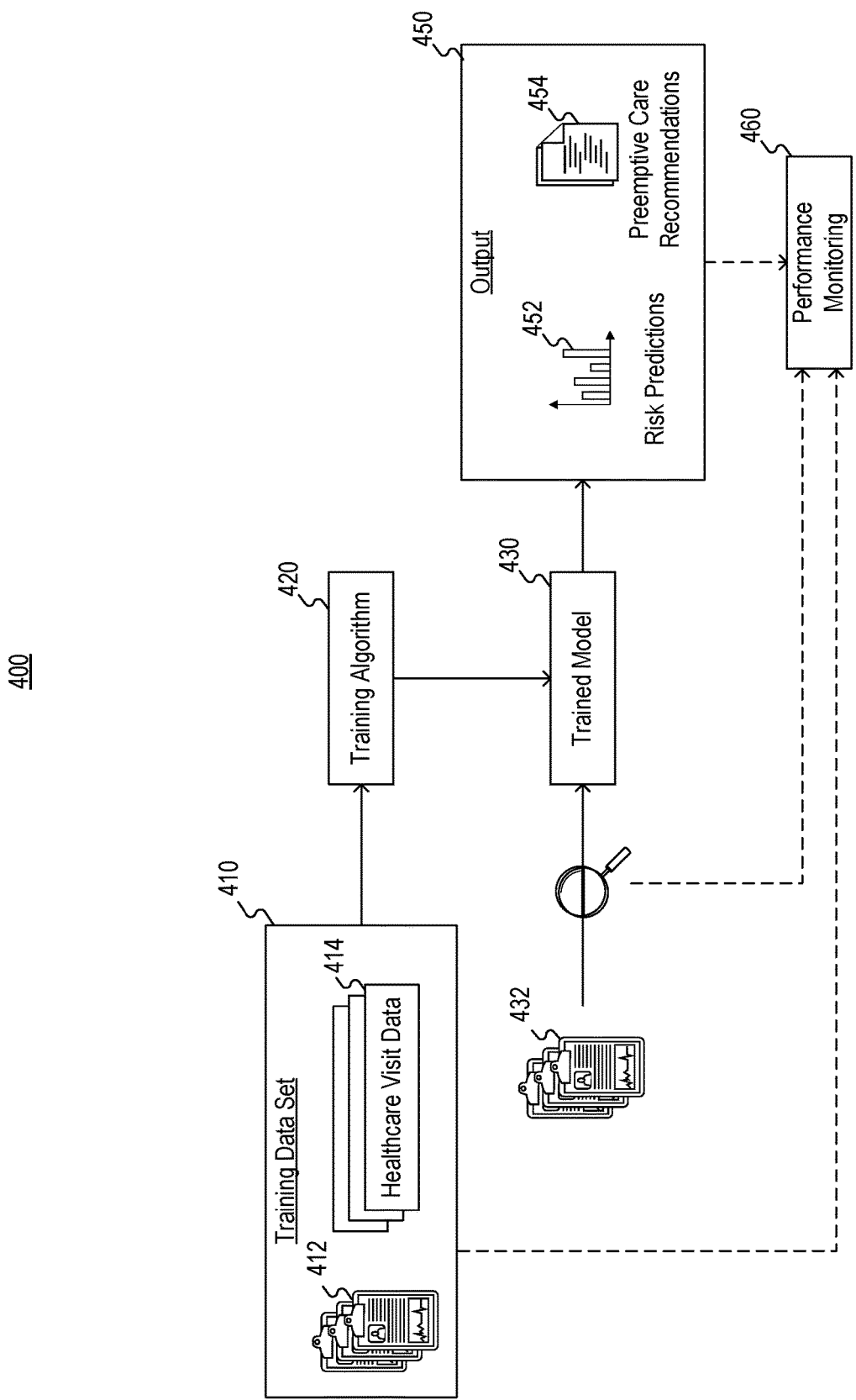
FIG. 4A illustrates an example machine learning system for implementing embodiments consistent with the present disclosure.

FIG. 4A illustrates an example machine learning system 400 for implementing embodiments consistent with the present disclosure. Machine learning system 400 may implemented as part of system 130 (as shown in FIG. 1). For example, machine learning system 400 may be a component of or a process performed using processing engine 131. In accordance with the disclosed embodiments, machine learning system 400 may develop and use a trained model to predict use of near-term patient medical services or a particular clinical outcome. For example, as shown in FIG. 4A, machine learning system 400 may construct a trained model 430 for identifying patients associated with a risk of a near term hospital service, acute service or other type of health service. Machine learning system 400 may develop model 430 through a training process, for example, using training algorithm 420.

Training of model 430 may involve the use of a training data set 410, which may be input into training algorithm 420 to develop the model. Training data 410 may include a plurality of patient medical records 412, which may include hospital services, acute health services or other type of health care services provided to patients associated with patient medical records 412. As an illustrative example, each of medical records 412 may be associated with an effective date (e.g., representing a simulated date the medical record may be accessed) and healthcare visit data 414 may indicate dates subsequent to the effective date that the patient required the hospital service, acute service or other type of health service. Accordingly, model 430 may be trained to associate various feature data within medical records 412 to subsequent hospital services, acute services, or other types of health services represented in healthcare visit data 414. In addition to predicting health care services likely to be provided for a patient based on severity or urgency for the patient or the type of facility or service provided, trained model 430 may be used to predict a wide variety of patient visits, treatment types, patient clinical outcomes or other purposes. Accordingly, the types of services the system is trained to predict may vary. In some embodiments, a physician or other healthcare provider may specify the types of services of interest. For example, a physician may be presented with a list of visit types (e.g., hospital visits, urgent care visits, etc.) or clinical outcomes, and the system may be configured to determine patient risk levels associated with the selected services or outcomes.

In some embodiments, training data 410 may also be cleaned, conditioned, and/or manipulated prior to input into training algorithm 420 to facilitate the training process. Machine learning system 400 may extract one or more features (or feature vectors) from the records and apply training algorithm 420 to determine correlations between the features and the subsequent medical visits. These features may be extracted from structured and/or unstructured data as described above with respect to FIG. 2. In some embodiments, the features may include demographic features, such as a patient's gender, race/ethnicity, sexual orientation, age, social indicators (e.g. income level, education level, food insecurity, access to housing and utility services, proximity to facility, access to caregiver) or other demographic information that may be included in a patient's medical data. In some embodiments, the features may include clinical data, such as indications of a patient's diagnosis, cancer stage (e.g., stage 4 breast cancer), comorbidities (e.g., heart disease), indications of adverse events (e.g., sepsis), lab tests and/or results (e.g., out of range albumin), vitals (e.g., weight, height, blood pressure, etc.), visits (e.g., visit to pain specialist), orders (e.g., antiemetic, pain agent), prescriptions, treatments, administrations (e.g., antineoplastic with high emetogenic potential), performance status (e.g. ECOG performance status), reported side effects, or any other clinical information that may be represented in structured or unstructured medical data. Trained model 430 may be trained to correlate such factors with actual health care usage or actual patient outcomes. In some cases, training of the model may result in model weights being assigned according to observed correlations between any of the model parameter inputs and health care usage (e.g., whether such usage occurs, when such usage occurs, a likelihood that such usage occurs, a probability that such usage occurs, etc.). In some cases, training of the model may result in model weights being assigned according to observed correlations between any of the model parameter inputs and occurrence of a particular clinical outcome (e.g., whether such outcome occurs, when such outcome occurs, a likelihood that such outcome occurs, a probability that such outcome occurs, etc.).

In some embodiments, the features used as inputs to training algorithm 420 may be weighted based on an expected degree of relevance as to whether a patient will use a particular near-term medical services or experience a near-term clinical outcome. For example, features such as particular diagnoses or previous use of a particular medical service or use of any medical services generally may be identified as having a higher expected relevance to predicted future use of medical services than others. Similarly, features such as particular diagnoses or previous use of a particular medical service or use of any medical services generally may be identified as having a higher expected relevance to predicted experience of a particular clinical outcome than others. Accordingly, training algorithm 420 may receive weights associated with one or more features as an input when training trained model 430. These weights may be determined in various ways. In some embodiments, medical care providers, such as physicians, nurses, researchers, insurance specialists, or other practitioners may be consulted to determine the weights. For example, the weights may be based on a survey, a poll, a focus group, an interview, a publication, or other form of input from medical providers.

In some embodiments, the weights may be defined by a logistic regression. The magnitude of a feature's coefficient in the logistic regression may define its importance. For example, a greater magnitude may indicate a greater importance. In the context of a logistic regression, where all predictors are binary, the presence (i.e., a value of 1) of a predictor (e.g., presence of an abnormal lab) indicates an increase in the log odds of the outcome by the value of the coefficient. Therefore, if the coefficient is positive, this may represent an increased likelihood of observing a positive outcome for that observation, and, if negative, a decreased likelihood of observing that outcome, all other predictors being constant. Thus, the most positive values of coefficients are associated with the highest increases in probability of the outcome being positive (e.g., actually having an ER visit in 60 days). A predetermined number of predictors with the most positive coefficients (e.g., 10, 20, 30, . . . N predictors) may thus treated as top features associated with risk for the outcome and may be surfaced in the output. Various other methods, such as gradient boosted trees, a Shapley value, a Gini impurity, or other approaches may be used.

Once model 430 is constructed, input data, such as medical records 432, may be input to model 430. Medical records 432 may correspond to medical record 212 and/or 300, as described above. For example, medical records 432 may include structured and unstructured data associated with a plurality of patients, such that each patient is associated with one or more medical records. Trained model 430 may extract features (which may include, but are not limited to, those described above with respect to medical records 412) from medical records 432 to generate an output 450. In some embodiments, medical records 432 may be processed prior to input into trained model 430. This may include extracting features from unstructured and/or structured data, image analysis (e.g., optical character recognition (OCR)), natural language processing tools, or various other methods. In some embodiments, input to trained model 220 may include machine learning outputs from other systems. For example, machine learning output from other systems can include a metastatic Natural Learning Processing Model that is trained to predict a patient's risk of having a metastatic disease. The predicted probability of a patient having a particular metastatic disease can be provided as input to trained model 220.

Output 450 may include risk predictions 452, which may correspond to risk prediction 222 described above. Risk predictions 452 may identify patients associated with medical records 432 that are expected to require or use certain types of medical services (e.g., hospital-based or acute care) within a predetermined time period or identify patients who are likely to experience certain clinical outcomes within a predetermined time period. These risk predictions may be presented in various ways. In some embodiments, a particular patient's risk may be binary. For example, a patient may be designated as "high risk" or "low risk" (which may be represented as a 1 or 0, or in various other forms). In some embodiments, the risk may be indicated as a probability such as, for example, between 0 and 1 (e.g. patient has a probability of 0.67 for receiving hospital-based care within 60-days). In addition to (or as an alternative to) a likelihood a patient will receive near-term medical care, risk predictions 452 may include other predictions for a patient or group of patients. For example, this may include predicted inpatient admissions, ICU admissions, patient mortality, an adverse event (e.g., sepsis, febrile neutropenia, etc.), and/or a combination of the above. For example, risk predictions 452 may include an "acute care outcome" if a patient is predicted to have a hospital visit, an inpatient admission, or an ICU admission within a predetermined number of days.

In some embodiments, output 450 may include one or more reports, as described above. For example, the report may comprise a list of patients expected to use emergency or other medical services within a predetermined time period (e.g., patients having been designated as "high risk," etc.). In some embodiments, the report may include both "high risk" and "low risk" patients. For example, the report may include patients belonging to a particular group. This may include patients having a particular medical condition, patients of a particular medical provider, patients of particular demographics, etc. In some embodiments, the patients may be identified by provider system 210. For example, the patients may be identified as part of a particular query. In some embodiments, the report may only include patients exceeding a particular likelihood threshold (e.g., 50%, 60%, 70%, 80%, 90%, 99%, etc.) or confidence value threshold. In some embodiments, the threshold may be adjustable based on desired levels of efficiency and performance. For example, system 130 may be configured to receive user inputs to tune performance of the model, which may include adjusting the threshold likelihood for inclusion in the report.

In some embodiments, system 130 may be configured to generate one or more preemptive care recommendations 454 as part of output 450. Preemptive care recommendations 454 may be a direct output of trained model 430 or may be generated as a subsequent step based on risk predictions 452. Preemptive care recommendations (also referred to herein as "recommended interventions") may include any temporal-based recommendations for treatment or care of a patient. For example, the preemptive care recommendations may include a recommended appointment with a particular care provider, an in-home patient visit, enrolling the patient in a particular treatment plan or facility, prescribing or refilling a prescription for a patient, providing a treatment to a patient, calling to check in with the patient, or any other event associated with care of the patient that may be scheduled. In some embodiments, the preemptive care recommendation may be expected to negate or reduce the risk of an undesirable near-term medical service for the patient (e.g., hospital-based care) or to negate or reduce the risk of an undesirable near-term clinical outcome. For example, trained model 430 may determine that certain features in medical records 432 indicate that a patient is expected to use hospital-based care within the next 90 days. Accordingly, system 130 may schedule a preventative treatment, a check-up or other preemptive care that may reduce the risk of the undesirable near-term medical service or clinical outcome.

In some embodiments, the preemptive care recommendation may be represented as general recommendations for a patient visit (e.g., flagging the patient for a near-term visit, etc.). In some embodiments, the preemptive care recommendation may include a specific date or date range in which a patient visit or other preemptive care is recommended. For example, the preemptive care recommendation may be to schedule a patient visit or preventative treatment at a particular date and/or time (e.g., next Tuesday at 9:00 AM). In some embodiments, preemptive care recommendations may be developed for multiple patients. For example, system 130 may develop a schedule for visiting each of the patients in the upcoming weeks. Accordingly, system 130 may be configured to generate scheduling recommendations such that each patient is seen at a different time to avoid conflicts. In some embodiments, the scheduling recommendations may be for a particular practitioner or caregiver. For example, if a clinic has three caregivers that provide in-home visits, scheduling recommendations may allocate patients included in the report to one of the three caregivers and may generate separate schedules for each of the three caregivers. This may include optimizing the schedule based on various factors. For example, the schedule may be developed so that a particular caregiver sees patients located within a predetermined distance of each other in the same day, or various other optimizations. In some embodiments, system 130 may access a current schedule of a healthcare provider and/or patient, and may generate the scheduling requirements based on the current schedule (e.g., to avoid conflicts, to reschedule other events, or the like).

In some embodiments, the report and/or the preemptive care recommendations (e.g., scheduling a patient visit) may be developed based on a priority level for each patient. The priority level may be any information indicating a relative priority among the patients. The priority may be based on various factors. For example, patients more likely to use hospital-based or other type of medical services within a particular time period may be given higher priority. In some embodiments, trained model 430 may also output an expected date when a patient is expected to use near-term medical services. Accordingly, the priority may be based on how soon the patient is expected to require or use a medical service. The priority may be based on other factors, such as the patient's medical condition, a severity of the condition, an expected clinical outcome, an urgency of a procedure expected to be required by the patient, an urgency of an expected emergency or other service, the patient's age, or various other factors. The report may be sorted or filtered based on the priority level of the patients. In some embodiments, the preemptive care recommendations may also be based on the priority level. For example, an appointment schedule may automatically be generated to schedule visits with the highest priority patients before visits to patients with lower priorities.

In some embodiments, machine learning system 400 may include a performance monitoring component 460, which may correspond to performance monitoring 230 described above with respect to FIG. 2. Performance monitoring component 460 may be configured to monitor inputs and/or outputs of model 430 to assess the performance of model 430. Performance monitoring can comprise, for example, data quality monitoring, performance monitoring of the predictions and bias monitoring of the predictions. In some embodiments, performance monitoring component 460 may be configured to detect anomalous inputs to model 430. For example, while model 430 may be trained such that it confidently predicts likelihoods of the use of near-term medical services or near-term clinical outcomes, anomalous input values may affect the results. Accordingly, as shown in FIG. 4A, performance monitoring component 460 may analyze inputs into model 430. This may include observing one or more of the features described above, such as prior usage of emergency services or medical services generally, medical diagnoses, lab results, vital signs, age, ethnicity, gender, stage of disease, prescribed medications, medication dosage, reported side effects, prescribed treatments, or any other relevant factors. Performance monitoring component 460 may perform a statistical analysis on these input features and detect anomalous values for these features.

In some embodiments, this may include tracking historical data for the input features and comparing current inputs to the historical data. This comparison may be performed in a variety of ways. In some embodiments, the statistical analysis may include keeping a running average (e.g., a simple moving average, an exponential moving average, a smoothed moving average, a linear weighted moving average, etc.) and comparing the current input to the moving average value. If the difference between the moving average value and the current input exceed a threshold degree of variation, the input may be marked as anomalous. While a moving average is provided by way of example, it is understood that various other statistical analyses may be used.

Alternatively, or in addition to detecting anomalous input values, performance monitoring 460 may analyze other potential causes of decreased performance of the model. In some embodiments, performance monitoring component 460 may detect stale data feeds, for example, by tracking a number of novel encounters for patients. This may also include determining whether selected subsets of data (e.g., tables) have become stale, for example, by tracking incremental row counts in source data feeds across tables. The performance may also be based on detecting lag with particular data fields, detecting inaccuracies in predictions, detecting bias in predictions, etc.

In some embodiments, performance monitoring 460 may include functionality for identifying and quantifying biases that may be trained into trained model 430. Based on this identification and quantification, an administrator or other user may correct trained model 430 to avoid generating biased predictions. Such biases may develop during the training process for trained model 430, as described above with respect to FIG. 4A. For example, in some cases, training data set 410 may inadvertently reflect inherent social biases associated with medical care, such as unequal access to medical care among ethnic or other groups. Because trained model 430 is developed based on this data, it may "learn" this inequality and may include biases in predicting medical care usage among different races or other social groups.

Figure 4B:
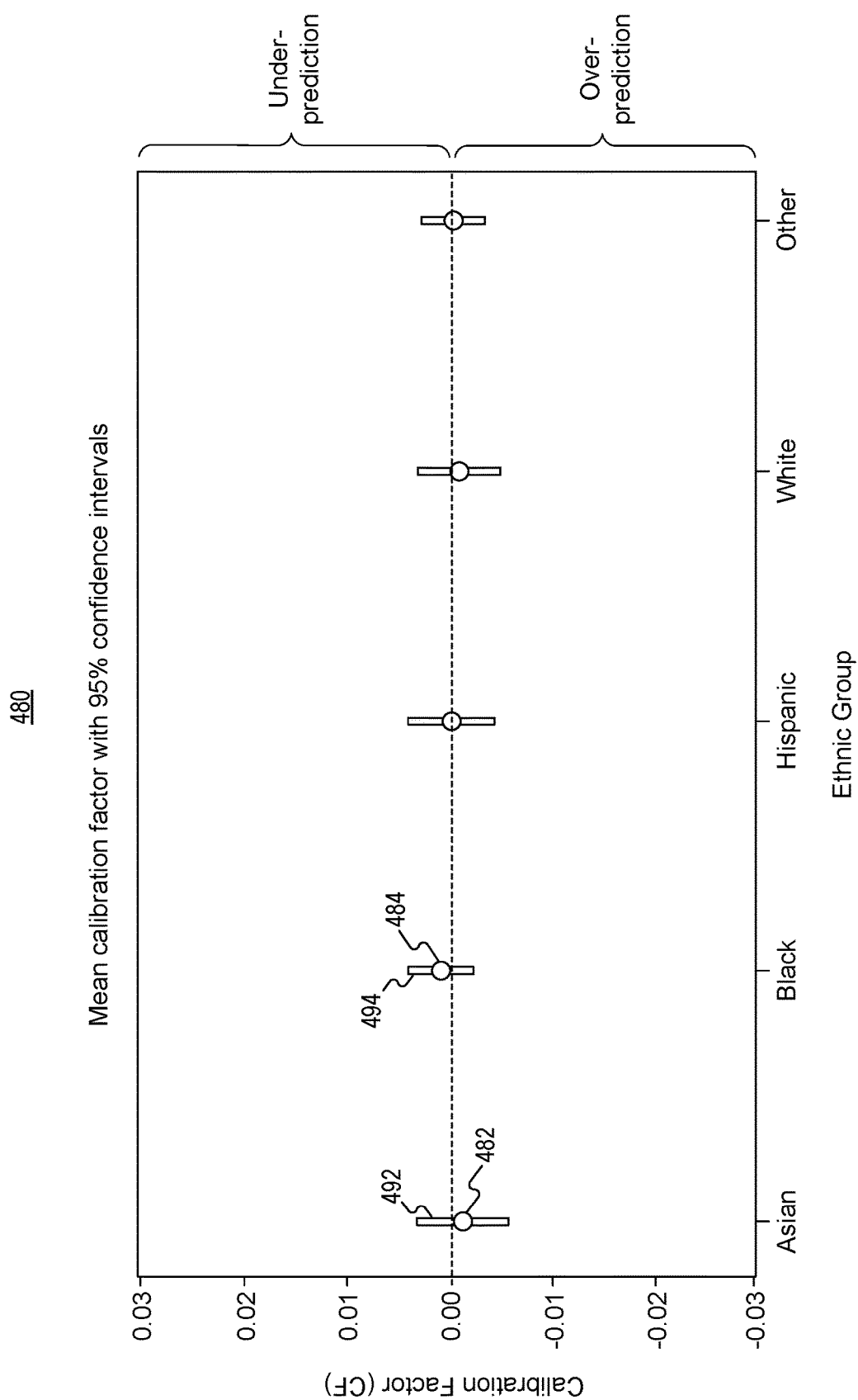
FIG. 4B illustrates example bias monitoring that may be performed using performance monitoring system 460 consistent with the disclosed embodiments.

To avoid perpetuating biases from the training data set 410 into risk predictions 452 and/or preemptive care recommendations 454, performance monitoring system 460 may analyze output 450 to quantify potential biases among various groups. FIG. 4B illustrates example bias monitoring 480 that may be performed using performance monitoring system 460 consistent with the disclosed embodiments. This monitoring may include determining a calibration factor for a plurality of groups of patients. For example, as shown in FIG. 4B, calibration factors may be determined for a plurality of ethnic groups (e.g., Asian, Black, Hispanic, White, Other, etc.). The calibration factor may be defined as CF= (Avg. ER Use)–(Avg. Predicted Risk) for each group of interest, where CF is the calibration factor, which represents the difference between the average usage of a particular medical service (e.g., hospital or acute medical services) minus the average predicted risk of the particular medical services within the group. These values may be determined retrospectively to verify the accuracy of model 430.

Ideally, the calibration factor (CF) would be zero for any given group, indicating the model is accurately predicting risk for the group. A non-zero calibration factor may indicate that the model is inaccurately predicting risk for the group, which may indicate a bias in the model, especially when the calibration factor for one group varies as compared to other groups. A calibration factor greater than zero may indicate the model is systematically underpredicting risk for a particular group, where a calibration factor less than zero may indicate the model is systematically over-predicting risk for the group. For example, calibration factor 482 may indicate an overprediction, whereas calibration factor 484 may indicate an underprediction. In some embodiments, performance monitoring system 460 may also determine other statistical values associated with the calibration factors, such as confidence intervals 492 and 494. For example, confidence intervals 492 and 494 may represent a range in which the model has a confidence level of 95% (or various other confidence levels, such as 99%, 90%, etc.) that the true calibration factor is within the range. The calibration factors and/or confidence intervals may be determined using stratified sampling or any other suitable sampling methods.

Based on the determined calibration factors, biases in the model may be identified and addressed. For example, an administrator may recognize a systematic bias in underpredicting risk associated with calibration factor 484 and may take necessary remedial action. For example, this may include re-training the model, applying a correction factor to one or more variables within the model, flagging the predictions associated with this group, generating an alert (e.g., to client devices 110, provider system 210, etc.) or various other control actions that may be performed. While FIG. 4B illustrates calibration-factors associated with racial biases, performance monitoring system 460 may similarly monitor for biases based on other groups, including gender, sexual orientation, ethnicity, religion, social class, or various other groups.

In some embodiments, bias can be avoided or minimized by monitoring training data sets 410 and medical records 432 and appropriately selecting data and medical records for inclusion into training data set 410. For example, by choosing medical records associated with patients where the included outcomes are more direct proxies for risk and better capture patients' health, by using a sub-cohort of a given patient group that has a high degree of data completeness. In further embodiments, a variable may be introduced into trained model 430 for a given patient group, while examining the coefficients associated with that group.

In some embodiments, performance monitoring can be achieved by examining the risk predictions against observed outcomes to track the accuracy of the predictions.

FIG. 5 is an illustration of an example report 500 identifying patients with heightened risk of a near-term use of particular medical services consistent with the disclosed embodiments. For example, report 500 may include a group of patients (identified as Patient 1, Patient 2, Patient 3, Patient 4, and Patient 5) having a likelihood of a use of near-term hospital-based medical services exceeding a particular threshold. Report 500 may be associated with a particular time period. For example, report 500 may include any patients having a risk of use of hospital-based medical services visit within a predetermined window (e.g., the next week, the next 30 days, the next 60 days, the next 90 days, etc.). This predetermined time window may be a default value, may be selected by a medical practitioner (e.g., through client devices 110), or may be defined in various other ways. In some embodiments, report 500 may include patients having recent encounters (e.g., recent medical visits, recent updates to their medical records, etc.). For example, this may include patients having an encounter in the last day, the last 3 days, the past week, past month, etc. In some embodiments, the patients in report 500 may be defined by provider system 210. For example, a query may define particular patients, a particular category of patients (e.g., including a particular feature), or the like.

Report 500 may include demographic information, such as the patient's gender or date of birth, as shown in FIG. 5. Various other demographic data may be included in report 500, such as the patient's race/ethnicity, gender, sexual orientation, an encounter date, a patient identifier, whether they are enrolled in Medicare, or various other information. In some embodiments, report 500 may be customizable such that a user may define which information is included.

Report 500 may also include information identifying or describe the basis for the predicted likelihood determination. For example, as shown in FIG. 5, report 500 may include a number of risk predictors and indicators (e.g., indicator 501) of whether the particular risk factor applies to each patient. In the example shown in FIG. 5, this may include vital signs associated with the patient, lab results, medical orders within a certain time period, patient visits, or diagnosis information. This may represent a predetermined number of the most relevant features to the trained model, as described above. In some embodiments, report 500 may also include an overall risk assessment indicating the patient's overall risk of near-term medical care. For example, report 500 may include an index, number, or numerical range indicative of a likelihood that an individual patient may make near term use of hospital-based or other medical services. Although not shown in FIG. 5, report 500 may also provide an estimate of a time, time range, etc. within which a particular patient may be predicted to make use of such near-term medical services. In some embodiments a similar report may be generated to identify patients with heightened risk of a near-term clinical outcome.

Figure 6:
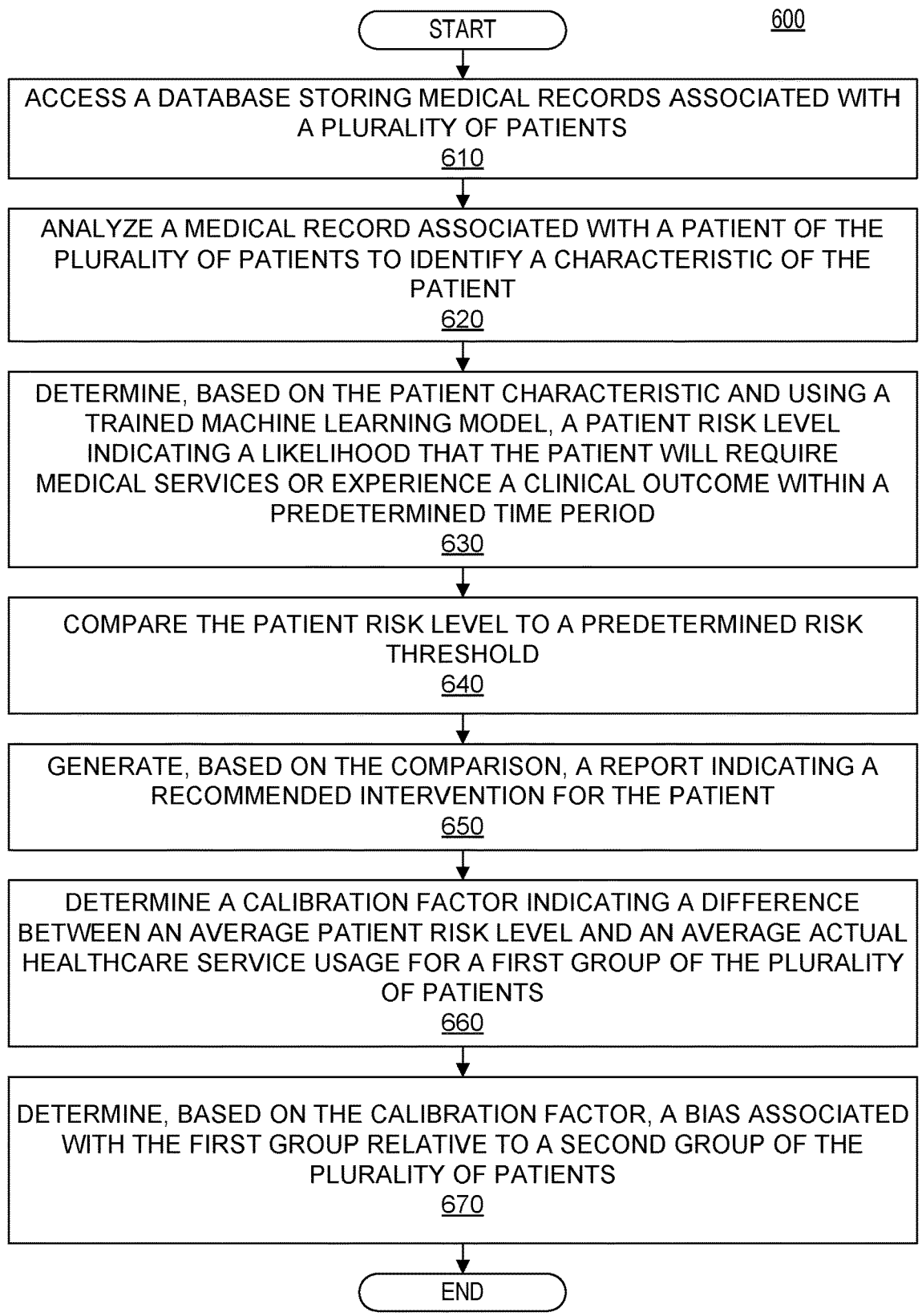
FIG. 6 is a flowchart showing an example process for predicting health care services, consistent with the disclosed embodiments.

FIG. 6 is a flowchart showing an example process 600 for predicting health care services or clinical outcomes, consistent with the disclosed embodiments. Process 600 may be performed by at least one processing device, such as processing engine 131, as described above. It is to be understood that throughout the present disclosure, the term "processor" is used as a shorthand for "at least one processor." In other words, a processor may include one or more structures that perform logic operations whether such structures are collocated, connected, or disbursed. In some embodiments, a non-transitory computer readable medium may contain instructions that when executed by a processor cause the processor to perform process 600. Further, process 600 is not necessarily limited to the steps shown in FIG. 6, and any steps or processes of the various embodiments described throughout the present disclosure may also be included in process 600, including those described above with respect to FIGS. 1-5.

In step 610, process 600 may include accessing a database storing a medical record associated with a patient. System 130 may access patient medical records from local database 132 or from an external data source, such as data sources 120. For example, medical record 212 may be provided by a provider system 210. The medical record may comprise one or more electronic files, such as text files, image files, PDF files, XLM files, YAML files, or the like. The medical records may include structured data (e.g., structured data 310) and/or unstructured data (e.g., unstructured data 320), as described above.

In step 620, process 600 may include analyzing the medical record to identify a characteristic of the patient. The characteristic of the patient may include any characteristic represented in the unstructured or structured data in the medical record. For example, the characteristic may include prior use of medical services by the patient, an indication of a medical diagnosis for the patient, a laboratory and/or diagnostic test result for the patient, a vital sign for the patient, or various other characteristics (e.g., features) described above. In some embodiments, the medical record may comprise structured data associated with the patient, as described above. Accordingly, analyzing the medical record may comprise analyzing the structured data. Similarly, the medical record may comprise unstructured data associated with the patient, and analyzing the medical record may comprise analyzing the unstructured data.

In step 630, process 600 may include determining, based on the patient characteristic and using a trained machine learning model, a patient risk level indicating a likelihood that the patient will require medical services within a predetermined time period or will experience a specific clinical outcome within a predetermined time period. For example, trained model 430 may be used to generate risk predictions 452, as described above with respect to FIG. 4. The predetermined time period may be any suitable period during which the use of medical services may be predicted based on medical record data. For example, the predetermined time period may be less than one week, less than one month, less than three months, or any other time period, as described above. In some embodiments, the predetermined time period may be defined as a default value. In other embodiments, the predetermined period may be a user-defined period (e.g., defined by a healthcare provider, administrator or other user, etc.). In some embodiments, the machine learning model being trained based on clinical factors weighted based on logistic regression. For example, a logistic regression or other weighting algorithm may be used to define a relative ranking for features input into training algorithm 420. As described above, the factors may be weighted based on input received through a survey, a focus group, a training process, or the like.

In step 640, process 600 may include comparing the patient risk level to a predetermined risk threshold. The predetermined risk threshold may be any value (e.g., a number, percentage, binary value, etc.) defining which patients should be included in a report. Accordingly, in step 650, process 600 may include generating, based on the comparison, a report indicating a recommended intervention for the patient. For example, system 130 may generate report 500 as an output of trained model 430, as described above. In some embodiments, process 600 may further include transmitting the report to a healthcare entity. For example, the report may be transmitted to provider system 210, as described above. The report may be configured to be displayed on a client device of the provider system, such as client devices 110. The recommended intervention for the patient may include any event associated with the care of the patient, as described above. For example, the recommended intervention may include a recommended treatment, patient evaluation, in-home care visit, prescription or refill, check-in call, or the like. The recommendation may be an explicit recommendation for an intervention (e.g., "Recommendation: perform in-home visit for "Patient 3" next Tuesday at 3:00 PM") or may be an implicit recommendation (e.g., by virtue of the patient being included in the report).

In step 660, process 600 may include determining a calibration factor indicating a difference between an average patient risk level and an average actual healthcare service usage for a first group of the plurality of patients. For example, the calibration factor may correspond to calibration factor 482 as described above with respect to FIG. 4B. The first group of patients may share a common trait or characteristic. In some embodiments, the common characteristic may be a common demographic classification, as described above. In some embodiments, step 660 may further include determining a confidence interval representing a range of values for the calibration factor associated with a particular degree of confidence. For example, the confidence factor may correspond to confidence factor 492 described above with respect to FIG. 4B.

In step 650, process 600 may include determining, based on the calibration factor, a bias associated with the first group relative to a second group of the plurality of patients. The second group of patients may have at least one trait or characteristic different from the first group. For example, first group may comprise patients having a first ethnicity and the second group comprises patients having a second ethnicity, as discussed above. In some embodiments, process 600 may perform additional actions based on detecting the bias. For example, process 600 may further include generating a report indicating the bias.

As described above, the system may further be configured to generate a schedule for patient visits or other recommended interventions. Accordingly, process 600 may further include scheduling at least one of a preemptive treatment, intervention or a visit for the patient based on the comparison with the threshold. In some embodiments, the recommended intervention may be intended to prevent or negate the need for the medical service. For example, if a patient is expected to require an emergency room visit for a particular adverse event, the recommended intervention may target conditions related to the adverse event to prevent the adverse event from occurring. In some embodiments, process 600 may further include generating, based on the patient risk level, a priority level for the patient, as described above. Accordingly, the recommended intervention may be scheduled based on the priority level. In some embodiments, generating the report may comprise including the patient in a list of a plurality of patients to receive an intervention within the predetermined time period. In such embodiments, the list may be organized based on at least one of predicted patient risk levels for the plurality of patients or predicted timeframes for medical services for the plurality of patients.

In some embodiments, the report may be generated for a plurality of patients. Accordingly, process 600 may further include generating reports indicating recommended interventions for a plurality of patients and scheduling, based on the reports, recommended interventions for the plurality of patients within the predetermined time period.

Figure 7:
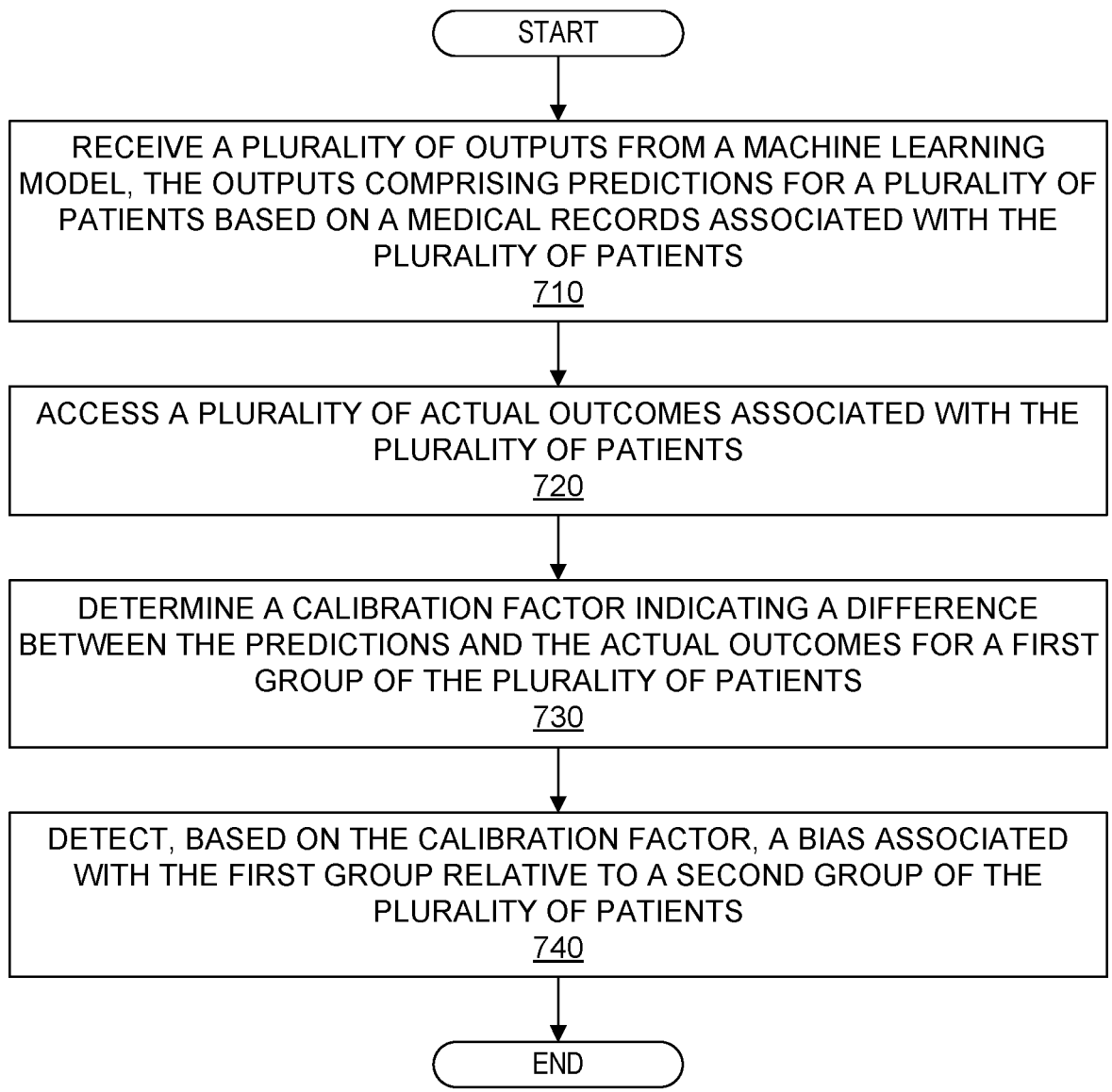
FIG. 7 is a flowchart showing an example process for evaluating a machine learning model, consistent with the disclosed embodiments.

FIG. 7 is a flowchart showing an example process 700 for evaluating a machine learning model for potential bias, consistent with the disclosed embodiments. Process 700 may be performed by at least one processing device, such as processing engine 131, as described above. Process 700 may be associated with the process performed by performance monitoring 460, as described above. In some embodiments, a non-transitory computer readable medium may contain instructions that when executed by a processor cause the processor to perform process 700. Further, process 700 is not necessarily limited to the steps shown in FIG. 7, and any steps or processes of the various embodiments described throughout the present disclosure may also be included in process 700, including those described above with respect to FIGS. 1-6.

In step 710, process 700 may include receiving a plurality of outputs from a machine learning model. The outputs may comprise predictions for a plurality of patients based on medical records associated with the plurality of patients. For example, the machine learning model may correspond to trained model 220 (or trained model 430) and accordingly, the outputs may correspond to output 224 (or output 450) as described above.

In step 720, process 700 may include accessing a plurality of actual outcomes associated with the plurality of patients. The actual outcomes may indicate whether the predictions for the plurality of patients included in the outputs were correct. For example, if the output includes a prediction of a risk of a patient requiring a particular medical service (such as risk prediction 452), the actual outcome may include an indication of whether the patient received the particular medical service. As another example, the outcome may include a predicted clinical outcome for a patient, and the actual outcome may indicate whether the patient experienced the predicted clinical outcome. Accordingly, the actual outcome data may be collected after the output has been generated. In some embodiments this may include accessing updated medical records for the plurality of patients. In some embodiments, the actual outcomes may be included in a training data set, such as training data set 410. Accordingly, process 700 may be performed during a training phase for a trained model.

In step 730, process 700 may include determining a calibration factor indicating a difference between the predictions and the actual outcomes for a first group of the plurality of patients. For example, step 730 may include determining calibration factor 482 as described above with respect to FIG. 4B. Accordingly, the calibration factor may represent the difference between an average usage of a particular medical service (e.g., hospital or acute medical services) minus the average predicted risk of the particular medical services within the first group. The group of patients may be defined based on a variety of characteristics. In some embodiments, the first group may include patients of a particular ethnic group (e.g., Asian, Black, Hispanic, White, Other, etc.). The first group may be determined based on other factors, such as gender, sexual orientation, ethnicity, religion, social class, or various other patient groups. In some embodiments, process 700 may include determining other statistical values associated with the calibration factor. For example, process 700 may further include determining a confidence interval representing a range of values for the calibration factor associated with a particular degree of confidence, such as confidence interval 492.

In step 740, process 700 may include detecting, based on the calibration factor, a bias associated with the first group relative to a second group of the plurality of patients. As noted above, the first and second groups may be selected on various social factors that may reflect a bias in the model. For example, the first group may comprise patients having a first ethnicity and the second group may comprise patients having a second ethnicity. Accordingly, the bias may reflect a bias based on ethnicity of patients inherent in the training data. This bias may be detected in various ways. In some embodiments, the bias may be detected based on a comparison of calibration factors between multiple groups. For example, process 700 may include determining an additional calibration factor indicating a difference between the predictions and the actual outcomes for the second group of the plurality of patients. For example, process 700 may include determining calibration factor 484 as described above with respect to FIG. 4B. Accordingly, detecting the bias may comprise comparing the calibration factor to the additional calibration factor.

In some embodiments, process 700 may include additional actions taken based on detecting the bias. For example, process 700 may include generating a report indicating the bias. For example, the report may be generated and transmitted to a user or other administrator, a healthcare provider, or the like. In some embodiments, process 700 may include providing a recommendation for at least one of: re-training the machine learning model, applying a correction factor, or flagging the plurality of outputs, as described above with respect to FIG. 4B.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, 4K Ultra HD Blu-ray, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, Python, R, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A model-assisted system for predicting health care services, the system comprising:
at least one processor programmed to:
access a database storing medical records associated with a plurality of patients;
analyze a medical record associated with a patient of the plurality of patients to identify a characteristic of the patient;
receive an indication of a selected type of health care service of interest, the selected type of health care service being selected by a user from a plurality of types of health care services;
determine, based on the patient characteristic and using a trained machine learning model, a patient risk level indicating a likelihood that the patient will require a health care service corresponding to the selected type of health care service within a predetermined time period relative to a date the medical record is accessed, the machine learning model being trained using a machine learning system configured to:
access training data comprising a plurality of training medical records, a simulated effective date for each of the plurality of training medical records, and a corresponding healthcare service date for each of the plurality of training medical records, the simulated effective date representing a simulated date each of the plurality of training medical records is accessed;
extract features from the plurality of training medical records; and
generate a model weight for each of the extracted features using a training algorithm;
compare the patient risk level to a predetermined risk threshold;
generate, based on the comparison, a report indicating a recommended intervention for the patient;
schedule the recommended intervention for the patient, the recommended intervention being scheduled based on a comparison of a priority level for the patient to a priority level of at least one additional patient of the plurality of patients;
determine a first calibration factor indicating a difference between an average patient risk level and an average actual healthcare service usage for a first group of the plurality of patients;
determine, based on a comparison of the first calibration factor to a second calibration factor associated with a second group of the plurality of patients, a bias associated with the first group relative to the second group of the plurality of patients; and
apply, based on the determined bias, a correction factor to at least one variable of the trained machine learning model.

2. The system of claim 1, wherein the medical record comprises structured data associated with the patient and analyzing the medical record comprises analyzing the structured data.

3. The system of claim 1, wherein the medical record comprises unstructured data associated with the patient and analyzing the medical record comprises analyzing the unstructured data.

4. The system of claim 1, wherein the patient characteristic comprises prior use of medical services by the patient.

5. The system of claim 1, wherein the patient characteristic comprises an indication of a medical diagnosis for the patient.

6. The system of claim 1, wherein the patient characteristic comprises at least one of a laboratory or diagnostic test result for the patient.

7. The system of claim 1, wherein the at least one processor is further configured to generate the priority level for the patient based on the patient risk level.

8. The system of claim 1, wherein the at least one processor is further configured to:
generate reports indicating recommended interventions for the plurality of patients; and
schedule, based on the reports, the recommended interventions for the plurality of patients within the predetermined time period.

9. The system of claim 1, wherein the at least one processor is further configured to generate a report indicating the bias.

10. The system of claim 1, wherein the first group comprises patients having a first ethnicity and the second group comprises patients having a second ethnicity.

11. The system of claim 1, wherein the at least one processor is further configured to determine a confidence interval representing a range of values for the first calibration factor associated with a particular degree of confidence.

12. A computer-assisted method for predicting health care services, the method comprising:
- accessing a database storing a medical record associated with a patient;
- analyzing the medical record to identify a characteristic associated with the patient;
- receiving an indication of a selected type of health care service of interest, the selected type of health care service being selected by a user from a plurality of types of health care services;
- determining, based on the patient characteristic and using a trained machine learning model, a patient risk level indicating a likelihood that the patient will require a health care service corresponding to the selected type of health care service within a predetermined time period relative to a date the medical record is accessed, the machine learning model being trained using a machine learning system configured to:
  - access training data comprising a plurality of training medical records, a simulated effective date for each of the plurality of training medical records, and a corresponding healthcare service date for each of the plurality of training medical records, the simulated effective date representing a simulated date each of the plurality of training medical records is accessed;
  - extract features from the plurality of training medical records; and
  - generate a model weight for each of the extracted features using a training algorithm;
- comparing the patient risk level to a predetermined risk threshold;
- generating, based on the comparison, a report indicating a recommended intervention for the patient;
- scheduling the recommended intervention for the patient, the recommended intervention being scheduled based on a comparison of a priority level for the patient to a priority level of at least one additional patient of the plurality of patients;
- determining a first calibration factor indicating a difference between an average patient risk level and an average actual healthcare service usage for a first group of the plurality of patients;
- determining, based on a comparison of the first calibration factor to a second calibration factor associated with a second group of the plurality of patients, a bias associated with the first group relative to the second group of the plurality of patients; and
- applying, based on the determined bias, a correction factor to at least one variable of the trained machine learning model.

13. The method of claim 12, wherein the medical record comprises structured data associated with the patient and analyzing the medical record comprises analyzing the structured data.

14. The method of claim 12, wherein the medical record comprises unstructured data associated with the patient and analyzing the medical record comprises analyzing the unstructured data.

15. The method of claim 12, wherein the patient characteristic comprises prior use of medical services by the patient.

16. The method of claim 12, wherein the patient characteristic comprises an indication of a medical diagnosis for the patient.

17. The method of claim 12, wherein the patient characteristic comprises at least one of a laboratory or diagnostic test result for the patient.

18. The method of claim 12, wherein the method further comprises generating the priority level for the patient based on the patient risk level.

19. The method of claim 12, wherein the method further comprises:
- generating reports indicating recommended interventions for the plurality of patients; and
- scheduling, based on the reports, recommended interventions for the plurality of patients within the predetermined time period.

* * * * *